United States Patent
Yoshimura et al.

(10) Patent No.: US 11,827,592 B2
(45) Date of Patent: Nov. 28, 2023

(54) ZINC CARBOXYLIC ACID SALT AND ZINC CARBOXYLATE SOLUTION CONTAINING SAME

(71) Applicant: NOF CORPORATION, Tokyo (JP)

(72) Inventors: Takeshi Yoshimura, Amagasaki (JP); Hiroyuki Ogi, Amagasaki (JP); Mako Iwasaki, Amagasaki (JP)

(73) Assignee: NOF CORPORATION, Tokyo (JP)

(*) Notice: Subject to any disclaimer, the term of this patent is extended or adjusted under 35 U.S.C. 154(b) by 0 days.

(21) Appl. No.: 17/920,193

(22) PCT Filed: Apr. 23, 2020

(86) PCT No.: PCT/JP2020/017440
§ 371 (c)(1),
(2) Date: Oct. 20, 2022

(87) PCT Pub. No.: WO2021/214927
PCT Pub. Date: Oct. 28, 2021

(65) Prior Publication Data
US 2023/0183162 A1   Jun. 15, 2023

(51) Int. Cl.
*C07C 57/12* (2006.01)
*C07C 53/126* (2006.01)
*C08K 5/098* (2006.01)

(52) U.S. Cl.
CPC ............ *C07C 57/12* (2013.01); *C07C 53/126* (2013.01); *C08K 5/098* (2013.01)

(58) Field of Classification Search
CPC ........ C07C 57/12; C07C 53/126; C08K 5/098
See application file for complete search history.

(56) References Cited

U.S. PATENT DOCUMENTS

| 4,235,794 A * | 11/1980 | Rieber ................. C07C 51/412 106/504 |
| 7,691,791 B2 * | 4/2010 | Usami ................ C10M 169/041 508/108 |
| 8,460,632 B2 | 6/2013 | Kang et al. |
| 2017/0306227 A1 * | 10/2017 | Ippen ..................... C09K 11/70 |
| 2018/0119007 A1 | 5/2018 | Ippen et al. |

FOREIGN PATENT DOCUMENTS

| CN | 110452684 A | 11/2019 | |
| EP | 2886594 A1 * | 6/2015 | ............. C08K 5/098 |
| JP | 2001-208118 A | 8/2001 | |
| JP | 2007-145993 A | 6/2007 | |
| JP | 2011-194562 A | 10/2011 | |
| JP | 2012-133111 A | 7/2012 | |
| JP | 2012-1333111 A1 * | 7/2012 | ............. G03G 5/147 |
| JP | 2016-121296 A | 7/2016 | |
| JP | 2019-515338 A | 6/2019 | |
| JP | 2020-070274 A | 5/2020 | |

OTHER PUBLICATIONS

International Search Report for PCT/JP2020/017440 dated Jul. 28, 2020.

* cited by examiner

*Primary Examiner* — Yate' K Cutliff
(74) *Attorney, Agent, or Firm* — Sughrue Mion, PLLC

(57) ABSTRACT

A composition of zinc salts of carboxylic acids. The carboxylic acids of the zinc salts include 0.5 to 6.0 mass % of a component (A), 0.05 to 1.2 mass % of a component (B) and 88.0 to 98.0 mass % of a component (C) described below. A ratio [(A)/(B)] of a mass of the component (A) with respect to a mass of the component (B) is 99/1 to 75/25, where (A) is a straight chain and saturated carboxylic acid having a carbon number of 12 to 22; (B) is a strait chain and unsaturated carboxylic acid having one unsaturated bond and a carbon number of 18, said unsaturated bond comprising a trans-form double bond; and (C) is a straight-chain and unsaturated carboxylic acid having one unsaturated bond and a carbon number of 18, said unsaturated bond comprising a cis-form double bond.

2 Claims, No Drawings

ZINC CARBOXYLIC ACID SALT AND ZINC CARBOXYLATE SOLUTION CONTAINING SAME

This application is a National Stage of Application No. PCT/JP2020/017440 filed Apr. 23, 2020.

TECHNICAL FIELD

The present invention is related to metal salts of carboxylic acids in which the heat resistance (low color scale), stability of viscosity and stability of solubility of zinc carboxylate salts can be improved. The zinc carboxylate salts may be applied in applications in which the zinc carboxylate salts are dissolved in a solvent or oil or the zinc carboxylate salts themselves are molten during the manufacturing process, and the applications include a thickening agent of a grease used for preventing corrosion of metals, an additive for a lubricant oil, a precursor material of quantum dots of a semiconductor or the like.

BACKGROUND ARTS

In prior arts, it is well known that a metal salt of a carboxylic acid has been applied in applications in which a zinc salt of a carboxylic acid is dissolved or the zinc salt of carboxylic acid itself is molten during the manufacturing process, and the applications include a thickening agent of a grease used for preventing corrosion of metals, an additive for a lubricating agent, a precursor material for quantum dots of a semiconductor or the like.

For example, in the case of the thickening agent of a grease, parts are contacted with sliding or contacted with rotation so that surfaces of metals are abraded when a machine or system is operated. For preventing such abrasion or controlling the abrasion of the surfaces of the metals, zinc salts of carboxylic acids are applied.

According to patent document 1, it is described a grease composition composed of zinc stearate and a base oil whose viscosity index is 190 or lower and whose kinetic viscosity at 40° C. is 200 $mm^2$/s or higher.

Further, zinc oleate is applied as a precursor of zinc for obtaining quantum dots and molten at a high temperature for use as a reaction material. Further, Patent document 2 describes that zinc acetate and oleic acid are reacted in 1-octadecene at 120° C. for 1 hour to obtain solution of zinc oleate when zinc precursor solution is produced for obtaining the quantum dots.

PATENT DOCUMENTS (Patent document 1) Japanese Patent Publication No. 2016-121296A
(Patent document 2) Japanese Patent Publication No. 2011-194562A

SUMMARY OF THE INVENTION

Objects to be Solved by the Invention

However, according to the grease composition described in patent document 1, although it is possible to reduce the sliding load and to impart high lubricating property, there is a problem of stability of solubility of a metal salt of carboxylic acid into a base oil under environmental condition of still higher viscosity range. Further, in the case of application in molten state, the color scale may be changed due to coloration or the change of the viscosity may be larger under agitating condition while the molten state is maintained, so that the quality may be deviated. Further, separation might be caused in the solution of zinc oleate described in patent document 2, so that the quantum dots of stable quality might not be obtained.

An object of the present invention is, in applications of dissolving zinc salts of carboxylic acids in a solvent or of melting the zinc salts, to improve the heat resistance (low color scale), stability of viscosity and stability of solubility of the zinc salts of carboxylic acids.

Solution for the Objects

As the present inventors have extensively researched for solving the objects described above, it is found that the heat resistance, stability of viscosity and stability of solubility of metal salts of carboxylic acids can be improved in applications that the metal salts are dissolved in a solvent and applied, in the case that the carboxylic acids forming the zinc salts of carboxylic acids have a specific composition. The present invention is thus made.

That is, the present invention provides (1) and (2).

(1) Zinc salts of carboxylic acids, wherein said carboxylic acids of said zinc salts comprise 0.5 to 6.0 mass % of a component (A), 0.05 to 1.2 mass % of a component (B) and 88.0 to 98.0 mass % of a component (C) described below, and wherein a ratio [(A)/(B)] of a mass of said component (A) with respect to a mass of said component (B) is 99/1 to 75/25.

(A) a straight chain and saturated carboxylic acid having a carbon number of 12 to 22

(B) a strait chain and unsaturated carboxylic acid having one unsaturated bond and a carbon number of 18, said unsaturated bond comprising a trans-form double bond (C) a straight chain and unsaturated carboxylic acid having one unsaturated bond and a carbon number of 18, said unsaturated bond comprising a cis-form double bond (2) A solution of zinc salts of carboxylic acids, said solution comprising said zinc salts of carboxylic acids of (1) and a solvent, wherein a total content of said zinc salts of carboxylic acids is 0.01 to 30 mass %.

Effects of the Invention

According to the present invention, in applications, such as a drying agent of a paint, additive for a lubricant oil, precursor material for quantum dots or the like, that zinc salts of carboxylic acids are dissolved in a solvent and then used, the heat resistance property, stability of viscosity and stability of solubility of the zinc salts of carboxylic acids of the present invention can be improved.

EMBODIMENTS FOR CARRYING OUT THE INVENTION (Zinc Salts of Carboxylic Acids)

The composition of carboxylic acids as raw materials of the alkali metal salts of carboxylic acids contains the component (A), component (B) and component (C) described above.

Here, the component (A) is a straight-chain and saturated carboxylic acid having a carbon number of 12 to 22. The carbon number of the straight-chain and saturated carboxylic acid may more preferably be 14 or higher and more preferably be 20 or lower. Further, the component (A) may be of a single kind or two or more kinds.

The component (B) is a straight-chain and unsaturated carboxylic acid having a carbon number of 18 and having a single unsaturated bond, and the unsaturated bond is a trans-form double bond. The carboxylic acid does not have a triple bond or cis-form double bond. Further, the component (B) may be of a single kind or two or more kinds.

Although the position of the trans-form double bond in the component (B) is not particularly limited, elaidic acid having a double bond at the 9'th position and vaccenic acid having a double bond at 11'th position are preferably listed, and elaidic acid is more preferred.

The component (C) is a straight-chain and unsaturated carboxylic acid having a carbon number of 18 and having a single unsaturated bond and the unsaturated bond is cis-form double bond. The carboxylic acid does not have a triple bond or trans-form double bond. Further, the component (C) may be of a single kind or two or more kinds.

Although the position of the cis-form double bond in the component (C) is not particularly limited, oleic acid having a double bond at the 9'th position or cis-vaccenic acid having double bond at 11'th position are preferably listed, and oleic acid is more preferred.

Provided that 100 mass % is assigned to a total content of the carboxylic acids forming the zinc salts of carboxylic acids, the content of the component (A) is made 0.5 to 6.0 mass %. As the thixotropic index of the thus obtained zinc salts of carboxylic acids becomes high and the stability of the solubility is deteriorated in the case that the content of the component (A) is lower than 0.5 mass %, the content is made 0.5 mass % or higher and may preferably be 1.5 mass % or higher. On the other hand, as the component (A) is precipitated during the dissolution and the stability is deteriorated in the case that the content of the component (A) exceeds 6.0 mass %, the content of the content (A) is made 6.0 mass % or lower and more preferably be 5.5 mass % or lower.

Provided that 100 mass % is assigned to a total content of the carboxylic acids forming the zinc salts of carboxylic acids, the content of the component (B) is made 0.05 to 1.2 mass %. The stability of the dissolution is thereby improved. On such viewpoint, the content of the component (B) may more preferably be 0.10 mass % or higher and more preferably be 1.0 mass % or lower.

Provided that 100 mass % is assigned to a total content of the carboxylic acids forming the zinc salts of carboxylic acids, the content of the component (C) is made 88.0 to 98.0 mass %. The color scale is thereby improved and the stability of the solubility is improved. On such viewpoint, the content of the component (C) may preferably be 89.0 mass % or higher and 95.0 mass % or lower.

According to the present invention, the ratio [(A)/(B)] of the mass of the component (A) with respect to the mass of the component (B) is made 99/1 to 75/25. The stability of the solubility is thereby improved. On such viewpoint, the mass ratio [(A)/(B)] may preferably be 98/2 to 80/20.

The carboxylic acids forming the composition of the zinc salts of carboxylic acids of the present invention may be consisting of the components (A), (B) and (C), or may further contain the other component (D) as a remainder in addition to the components (A), (B) and (C). That is, the content of the other component (D) is a remainder obtained by deducting the total content of the components (A), (B) and (C) from 100 mass %, and may preferably be 10 mass % or lower, more preferably be 5 mass % or lower and may be 0.0 mass %.

A carboxylic acid forming the other component (D) may have two or more double bonds and more preferably have two or three double bonds. Further, the carbon number of the carboxylic acid forming the other component (D) may preferably be 16 to 22, more preferably be 16 to 18, and most preferably be 18.

The double bond in the component (D) may be of cis-form or trans-form, and as to the position of the double bond, linoleic acid having cis-form double bonds at 9'th and 12'th positions, linoelaidic acid having trans-form double bonds at 9'th and 12'th positions and linolenic acid having cis-form double bonds at 9'th, 12'th and 15'th positions may be preferably listed. Linoleic acid and linolenic acid are more preferred, and linoleic acid is most preferred.

(Production Method of Zinc Salts of Carboxylic Acids)

As a main method of producing the metal salts of carboxylic acids, direct method and double decomposition method are listed. The direct method means a method that metal salts of carboxylic acids are obtained by direct reaction of molten carboxylic acids and a metal oxide or metal hydroxide. Further, the double decomposition method means a method that metal salts of carboxylic acids are obtained through the rection of aqueous solution of metal salts of carboxylic acids and an inorganic metal salt.

The direct method has advantages in a facility that the production steps are simple and the facility scale is small, and has the following problems as follows on the opposite side.

(a) The termination of the completion of the reaction is poor and much amounts of unreacted carboxylic acids and metal oxide or metal hydroxide as raw materials remain in the metal salts of carboxylic acids.

(b) The color scale of the metal salts of carboxylic acids is deteriorated as the reaction is performed at a high temperature.

(c) As the reactivity is poor and an equivalent molar amount or more of the metal oxide or metal hydroxide is reacted with carboxylic acids according to prior arts, basic metal salt (mono salt) of carboxylic acid is remained in the thus obtained metal salts of carboxylic acids, so that the melting point may be increased or the solubility may be lowered.

On the other hand, the double decomposition method has advantages in the quality that the contents of the unreacted carboxylic acids, metal compound as the raw material, heterogenous metals and the like are low, the color scale is good and fine powder is obtained, contrary to the direct method described above. On the other hand, the following problems are provided.

(a) A large production facility is necessary.
(b) The dispersion the reaction slurry into water is unstable and the workability is low.
(c) It is difficult to lower the water content of a product.

Each of the direct method and double decomposition method may be applied for producing the zinc salts of carboxylic acids of the present invention, and the zinc salts of carboxylic acids obtained by the double decomposition method is more preferred, on the viewpoint of improving the heat resistance and stability of viscosity in the molten state and of improving the stability of dissolution into a solvent.

As the monovalent alkaline compound as the raw material for the alkali metal salts of carboxylic acids, hydroxide of an alkali metal (sodium, potassium or the like) and an amine such as ammonia, mono-ethanol amine, di-ethanol amine, tri-ethanol amine or the like are listed. The hydroxide of an alkali metal such as sodium, potassium or the like is preferred, on the viewpoint of a high solubility in water and resistance against coloration when it is converted into the alkali metal salts of carboxylic acids. The monovalent alkali compound and carboxylic acids are reacted to obtain the alkali metal salts of carboxylic acids at a temperature, which is generally higher than the melting point of carboxylic acids and at which the carboxylic acids do not decompose, and preferably at a temperature of 40 to 85° C., more preferably at a temperature of 50 to 80° C. and most preferably 60 to 75° C.

The zinc salts of the divalent carboxylic acids of the present invention are metal salt powder of carboxylic acid obtained by reacting the alkali metal salts of carboxylic acids obtained as described above and a divalent zinc salt in aqueous solution. The divalent zinc salt is specifically a salt of a divalent zinc metal and an inorganic acid or organic acid. The divalent inorganic zinc salt may preferably be zinc sulfate, zinc chloride or zinc nitrate. Among them, zinc sulfate and zinc chloride are particularly preferred because they are easily available on industrial viewpoint.

The reaction described above is performed specifically by preparing aqueous solution containing the divalent zinc salt and aqueous solution containing the alkali metal salts of carboxylic acids separately and by mixing them. For example, it is performed by adding the aqueous solution containing the divalent zinc salt into the aqueous solution containing the alkali metal salts of carboxylic acids, or by adding the both into separate reaction baths.

When the aqueous solution containing the alkali metal salts of carboxylic acids and solution containing the divalent zinc salt are mixed, for example, if the aqueous solution containing the divalent zinc salt is charged into the aqueous solution containing the alkali metal salts of carboxylic acids in one batch, the shape of the thus obtained powder of the metal salts of carboxylic acids may be uneven and the distribution of particle size may be wide. Further, the precipitated zinc salts of carboxylic acids may be aggregated. It is thus preferred that the aqueous solution containing the divalent zinc salt is gradually added dropwise at an appropriate rate into the solution containing the alkali metal salts of carboxylic acids.

The concentration of the alkali metal salts of carboxylic acids during the production of the metal salts of carboxylic acids is usually 1 mass % to 20 mass % and preferably 5 mass % to 15 mass %, on the viewpoint of productivity of the metal salts of carboxylic acids and the handleability of the aqueous solution containing the alkali metal salts of carboxylic acids or the thus obtained slurry of metal salts of carboxylic acids. In the case that the concentration of alkali metal salts of carboxylic acids is less than 1 mass %, the productivity of the metal salts of carboxylic acids may be possibly lowered, which is not practically preferred. In the case that it exceeds 20 mass %, the viscosity of the aqueous solution containing the alkali metal salts of carboxylic acids or the thus obtained slurry of the metal salts of carboxylic acids is increased, so that uniform reaction may possibly be difficult.

Further, the concentration of the divalent zinc salt in the solution containing the divalent zinc salt is usually 10 mass % to 50 mass % and preferably 10 mass % to 40 mass %, on the viewpoint of productivity of the metal salts of carboxylic acids and of handleability of the aqueous solution containing the alkali metal salts of carboxylic acids or the thus obtained slurry of the metal salts of carboxylic acids.

The reaction of the alkali metal salts of carboxylic acids and divalent zinc salt is performed at a temperature lower than the softening point of the thus obtained metal salts of carboxylic acids, and the temperature may preferably be 40 to 85° C., more preferably be 50 to 80° C. on the viewpoint of solubility of the alkali metal salts of carboxylic acids. In the case that the reaction temperature is lower than 40° C., the reaction rate of the alkali metal salts of carboxylic acids and divalent zinc salt may be possibly lowered.

For stabilizing the slurry of the metal salts of carboxylic acids during the reaction of the alkali metal salts of carboxylic acids and divalent zinc salt and for improving the productivity of the metal salts of carboxylic acids, it is preferred that a polyalkylene glycol series ether, particularly triblock ether having structure (EO-PO-EO) with oxypropylene block is inserted between oxyethylene blocks, is contained in the slurry of the metal salts of carboxylic acids. The content of the polyalkylene glycol series ether in the slurry of the metal salts of carboxylic acids is usually, 0.01 mass parts to 5 mass parts and preferably 0.05 mass parts to 2 mass parts, with respect to 100 mass parts of the alkali metal salts of carboxylic acids. Further, the polyalkylene glycol series ether may be present in reaction system before the monovalent alkali compound and carboxylic acids are reacted or may be present in the reaction system before the alkali metal of carboxylic acid and divalent zinc salt are reacted.

The slurry of the metal salts of carboxylic acids is obtained according to the method described above. The slurry of the metal salts of carboxylic acids is subjected to separation of a solvent by itself or through a centrifugal dehydrator, a filter press, vacuum rotary filter or the like, and optionally subjected to cleaning to remove inorganic salts as byproduct, and then subjected to drying by means of a tray drier, rotary drier, air drier, ventilation drier, spray drier, fluidized bed drier or the like.

The method of drying may be continuous type or batch type, and may be performed under ambient pressure or vacuum. Further, the dried zinc salts of carboxylic acids are optionally crushed. The method of crushing is not particularly limited and may be performed by means of a pin mill, jet mill, atomizer or the like, for example. The crushed particles of the zinc salts of carboxylic acids are subjected to classification. That is, the particles are subjected to classification by means of multistage sieving system or the like of applying vibration to perform the sieving, so that the distribution of particle size is adjusted. The particles of the zinc salts of carboxylic acids of the present invention can be thereby obtained.

(Physical Properties of Zinc Salts of Carboxylic Acids)

On the viewpoint of dispersion into a solvent and stability of solubility, the stability of viscosity (a value of a viscosity at 1 rpm divided by a viscosity at 2.5 rpm of a sample molten at 100° C. and measured by a B-type viscometer) of the zinc salts of carboxylic acids of the present invention is 1.04 to 1.10 and preferably 1.04 to 1.09.

Further, on the viewpoint of heat resistance (low color scale), in the case that it is molten at 100° C., the Gardner color scale may preferably be 3 or lower and more preferably 2 or lower. Further, in the case that the molten state is maintained at 100° C. for 1 hour, the Gardner color scale may preferably be 4 or lower and more preferably be 3 or lower. As to the change of the color scales, the difference of the Gardner color scale after it is held for 1 hour and the Gardner color scale directly after it is molten may preferably be 2 or smaller and more preferably be 1 or smaller.

(Solution of Zinc Salts of Carboxylic Acids)

The solvent for dissolving the zinc salts of carboxylic acids of the present invention is not particularly limited, and may preferably be a non-polar solvent having a boiling point of 170° C. or higher on the viewpoint of the solubility of the zinc salts of carboxylic acids. For example, specifically, the non-polar solvent may be a fatty saturated hydrocarbon such as n-decane, n-dodecane, n-hexadecane, n-octadecane or the like; a fatty unsaturated hydrocarbon such as 1-undecene, 1-dodecene, 1-hexadecene, 1-octadecene or the like; tri-octyl phosphine or the like.

Among them, the fatty saturated hydrocarbon is preferred and that having a carbon number of 12 to 18 is more preferred.

In the solution of the zinc salts of carboxylic acids of the present invention, the zinc salts of carboxylic acids may preferably be contained in 0.01 to 30 mass %, provided that 100 mass % is assigned to a total content of the solvent and zinc salts of carboxylic acids.

EXAMPLES

The present invention will be described further in detail below, referring to inventive and comparative examples.

Inventive Example 1: Preparation of Zinc Salts of Carboxylic Acids 250 g of a composition of carboxylic acids having a composition of "No. 1" shown in table 1 and 2500 g of water were charged into 3-liter separable flask and the temperature was elevated to 70° C. 77.2 g of 48 mass % aqueous solution of sodium hydroxide was then added and agitated for 1 hour at the same temperature (70° C.) to obtain aqueous solution of alkali metal salts of carboxylic acids. Thereafter, while it was held at 70° C., 151.2 g of 25 mass % zinc chloride aqueous solution was added dropwise over 1 hour into the aqueous solution of the alkali metal salts of carboxylic acids. After the completion of the dropwise addition, it was further agitated over 1 hour at 70° C. 1500 g of water was added into the thus obtained slurry of aqueous solution of the zinc salts of carboxylic acids, which was then cooled to 60° C. or lower. Thereafter, the solution was filtered through a suction filtering machine, washed with 1000 g of water twice, and the thus obtained cakes were dried at 75° C. over 72 hours by means of a tray drier, ground and classified to obtain particles of the zinc salts of carboxylic acids.

Inventive Example 2

The carboxylic acid composition used was changed to "No. 2" shown in table 1. It was performed according to the same conditions as those of the inventive example 1.

Comparative Example 1

The carboxylic acid composition used was changed to "No. 3" shown in table 1. It was performed according to the same conditions as those of the inventive example 1.

Comparative Example 2

The carboxylic acid composition used was changed to "No. 4" shown in table 1. It was performed according to the same conditions as those of the inventive example 1.

Then, the viscosities at 100° C. (1 rpm and 2.5 rpm), the stability of the viscosities and heat resistance of each of particles of the zinc salts of carboxylic salts of the inventive examples 1 and 2 and comparative examples 1, 2 and 3 were measured as follows, respectively, and the results of measurement were shown in table 2.

(Viscosities at 100° C.)

The viscosities (1 rpm and 2.5 rpm) of a sample molten at 100° C. were measured by means of a B-type viscometer.

(Stability of Viscosity)

A value obtained by dividing the viscosity at 1 rpm with the viscosity at 2.5 rpm.

(Heat Resistance)

Color scale direct after a sample was completely molten at 100° C. and color scale after the sample was held in molten state for 1 hour at 100° C. were measured as Gardner color scale. The Gardner scales of the respective samples direct after the melting were proved to be 2. Table 2 shows the color scales after the samples were held for 1 hour. Further, a difference of the color scale direct after the melting and color scale after the sample was held for 1 hour was calculated and shown in a parenthesis shown in table 2. Further, the measurement was performed based on JIS K-0071-2.

(Production and Evaluation of Solution of Zinc Salts of Carboxylic Acids)

800.0 g of 1-octadecene and 200.0 g of the zinc salts of carboxylic acids of the respective examples shown in table 2 were charged into 2 liter round bottle flask made of SUS and mixed under nitrogen bubbling at 300° C. for 5 hours to obtain solutions. After the mixing, the temperature of the solution was cooled to room temperature to obtain a sample.

The stability of solubility of the thus obtained sample was confirmed by eyes. The results were shown in table 3.

TABLE 1

| | | Carbon number | | | | | | | | | |
| --- | --- | --- | --- | --- | --- | --- | --- | --- | --- | --- | --- |
| | | 16 | 18 | 18 | 18 | 18 | 18 | | | | |
| | | | | Number of double | | | | | | | |
| | | 0 | 0 | 1 cis | 1 Trans | 2 cis | 3 Cis | | | | |
| | | | | Position of Double bonds | | | | | | | |
| | | — | — | 9-position | 9-position | 9-position 12-position | 9-position 12-position 15-position | | | | |
| | | | | Components | | | | Component | Component | Component | |
| | | (A) | (A) | (C) | (B) | (D) | (D) | (A) | (B) | (C) | (A)/(B) |
| Composition of carboxylic acids | No. 1 | 3.10 | 1.40 | 92.17 | 0.16 | 2.85 | 0.32 | 4.50 | 0.16 | 92.17 | 97/3 |
| | No. 2 | 2.23 | 0.87 | 93.31 | 0.70 | 2.37 | 0.52 | 3.10 | 0.70 | 93.31 | 82/18 |
| | No. 3 | 0.24 | — | 99.44 | — | 0.32 | — | 0.24 | 0.00 | 99.44 | 100/0 |
| | No. 4 | 1.36 | 2.76 | 89.45 | 2.12 | 4.31 | — | 4.12 | 2.12 | 89.45 | 66/34 |

TABLE 2

| Raw material Carboxylic acids | | Viscosity at 100° C. (1.0 rpm) | Viscosity as 100° C. (2.5 rpm) | Stability of viscosity | Color scale (Gardner) |
|---|---|---|---|---|---|
| (Inventive Example 1) Zinc carboxylates 1 | No. 1 | 878.8 | 802.6 | 1.09 | 3 (Δ1) |
| (Inventive Example 2) Zinc carboxylates 2 | No. 2 | 854.5 | 798.3 | 1.07 | 3 (Δ1) |
| (Comparative Example 1) Zinc carboxylates 3 | No. 3 | 884.6 | 790.2 | 1.12 | 3 (Δ1) |
| (Comparative Example 2) Zinc carboxylates 4 | No. 4 | 867.9 | 780.2 | 1.11 | 5 (Δ3) |

TABLE 3

| | Raw material: Zinc carboxylate | Stability of Solubility |
|---|---|---|
| Inventive Example 1 | Zinc carboxylates 1 | ○ |
| Inventive Example 2 | Zinc carboxylates 2 | ○ |
| Comparative Example 1 | Zinc carboxylates 3 | Separated |
| Comparative Example 2 | Zinc carboxylates 4 | Muddy |

As shown in tables 1 to 3, in the case that carboxylic acids forming the zinc salts of carboxylic acids satisfy the composition of the present invention, the stability of viscosity and heat resistance of the molten substance of the zinc salts of carboxylic acids were good, and the stability of the solubility of the solution of zinc salts of carboxylic acids was high.

According to the comparative example 1, as the ratios of the components (A) and (B) and (A)/(B) were out of the present invention, the stability of the viscosity was low and the separation of zinc salts of carboxylic acids was observed.

According to the comparative example 2, as the ratios of the component (B) and (A)/(B) were out of the present invention, the stability of the viscosity was low, the color scale after 1 hour was considerably changed and muddy appearance was observed in the solution.

The invention claimed is:

1. A composition of zinc salts of carboxylic acids, wherein said carboxylic acids of said zinc salts comprise 0.5 to 6.0 mass % of a component (A), 0.05 to 1.2 mass % of a component (B) and 88.0 to 98.0 mass % of a component (C) described below, and wherein a ratio [(A)/(B)] of a mass of said component (A) with respect to a mass of said component (B) is 99/1 to 75/25:
   (A) is a straight chain and saturated carboxylic acid having a carbon number of 12 to 22;
   (B) is a strait chain and unsaturated carboxylic acid having one unsaturated bond and a carbon number of 18, said unsaturated bond comprising a trans-form double bond; and
   (C) is a straight-chain and unsaturated carboxylic acid having one unsaturated bond and a carbon number of 18, said unsaturated bond comprising a cis-form double bond.

2. A solution of a composition of zinc salts of carboxylic acids, said solution comprising said composition of zinc salts of carboxylic acids of claim 1 and a solvent, wherein a total content of said composition of zinc salts of carboxylic acids is 0.01 to 30 mass %.

* * * * *